United States Patent
Hayama et al.

[11] Patent Number: 6,123,933
[45] Date of Patent: Sep. 26, 2000

[54] HAIR COSMETIC COMPOSITIONS

[75] Inventors: Kazuhide Hayama; Yasuo Kitani; Tomoaki Hiwatashi, all of Yokkaichi, Japan

[73] Assignee: Mitsubishi Chemical Corporation, Tokyo, Japan

[21] Appl. No.: 08/682,239

[22] Filed: Jul. 17, 1996

[30] Foreign Application Priority Data

Jul. 19, 1995 [JP] Japan ................................. 7-204027

[51] Int. Cl.⁷ ..................................... A61K 7/035
[52] U.S. Cl. ........................ 424/69; 424/70.1; 424/70.11; 514/880
[58] Field of Search ................. 424/69, 70.1, 70.11; 514/880

[56] References Cited

U.S. PATENT DOCUMENTS

| | | | |
|---|---|---|---|
| 4,013,787 | 3/1977 | Varlerberghe | 424/70 |
| 4,533,545 | 8/1985 | Sebag | 424/70 |
| 4,767,616 | 8/1988 | Mitsubishi | 424/70 |
| 4,900,545 | 2/1990 | Wisotzki et al. | 424/70 |
| 4,923,977 | 5/1990 | Lang et al. | 536/20 |

FOREIGN PATENT DOCUMENTS

| | | |
|---|---|---|
| 2072185 | 12/1992 | Canada . |
| 201342 | 11/1986 | European Pat. Off. . |
| 521666 | 1/1993 | European Pat. Off. . |
| 50-160393 | 12/1975 | Japan . |
| 51-23530 | 2/1976 | Japan . |
| 53-15436 | 2/1978 | Japan . |
| 53-121946 | 10/1978 | Japan . |
| 2043077 | 10/1980 | United Kingdom . |

*Primary Examiner*—Terressa Mosley-Boykin
*Attorney, Agent, or Firm*—Sughrue, Mion, Zinn, Macpeak & Seas, PLLC

[57] ABSTRACT

A hair cosmetic composition comprising an amine-oxide-containing water-soluble resin having a weight-average molecular weight of 5,000 to 1,000,000. The hair cosmetic composition of the present invention has excellent setting force, conditioning effects and hair-washing property and being free from stickiness.

21 Claims, No Drawings

HAIR COSMETIC COMPOSITIONS

FIELD OF THE INVENTION

The present invention relates to a hair cosmetic composition comprising an amine-oxide-containing water-soluble resin. The hair cosmetic composition according to the present invention is excellent in adhesion to hair and compatibility with various base materials, has good water-solubility and provides an film for excellent hair setting force and touch feeling.

BACKGROUND OF THE INVENTION

It is known that hair in a desired form is obtained by conducting hair setting using a resin.

As resins for hair cosmetics having such a purpose, nonionic, anionic and cationic resins are employed.

Examples of the nonionic resin used for the hair cosmetics include polyvinyl methyl ether, polyvinyl pyrrolidone and the like. Polyvinyl pyrrolidone is susceptible to the influence of humidity conditions. Described specifically, before moisture absorption, its film is hard and tends to cause a flaking phenomenon, while under high-temperature and high-humidity conditions, it becomes extremely flexible and causes a blocking phenomenon. There is therefore a potential danger that hairs stick to each other and it becomes impossible to comb or brush them. Polyvinyl methyl ether is much more susceptible to humidity.

Examples of the anionic resin include copolymers of a vinylcarboxylic acid, as an ionic group, such as acrylic acid and methacrylic acid with styrene, an alkyl acrylate or the like. Different from the nonionic resin, the anionic resin is less influenced by humidity, but because having an anionic property similar to hair, its affinity for hair is weak. In addition, the film of the anionic resin is fragile in spite of being hard and having high hair-conditioning effects so that there is a potential danger of occurring a flaking phenomenon. Moreover, the use of an anionic resin restricts the addition of a cationic substance, thereby possibly causing a solidifying phenomenon when a hair rinse (cationic-base) is used at the time of hair washing.

The cationic resin has a stronger affinity for hair than the former two resins, but is susceptible to humidity as in the nonionic resin. In addition, it is accompanied with the problems such as fears of toxicity and irritation to skin resulting from its cationic property, a limitation to the addition of the anionic resin and a solidifying phenomenon at the time when a shampoo (anionic-base) is used upon hair washing.

There is increasingly a demand for a hair cosmetic composition which can be removed easily by washing of the hair, can be readily diluted with water upon its preparation, and is free from an alcohol content in view of an environmental problem. It is therefore preferred that the resin to be employed is water soluble. In general, an increase in the water solubility of the resin, however, leads to a problem that the setting force lowers.

As a hair cosmetic composition which overcomes the defects of those containing the anionic resin, cationic resin or nonionic resin, an amphoteric ion polymer, that is, a copolymer containing as a hydrophilic group a carboxybetaine fracture has been proposed. The amphoteric ion polymer is known as a hair conditioning polymer excellent in performances such as affinity for hair and setting force. The amphoteric ion polymer proposed is a hair conditioning resin composed of an amphoteric polymer obtained by converting into, a corresponding amphoteric polymer, a terpolymer of (a) a tertiary-amine-containing (meth)acrylate (the term "(meth)acrylic acid" will hereinafter embrace both acrylic acid and methacrylic acid) base unsaturated monomer, (b) a $C_{1-4}$ alkyl (meth)acrylate and (c) a $C_{12-18}$ alkyl (meth)acrylate, with a halogenated acetate (refer to JP-A-51-9732 and JP-A-55-104209) (the term "JP-A" as used herein means an "unexamined published Japanese patent application").

However, the above amphoteric ion polymer has not a sufficient compatibility with various cosmetic base materials, for example, an anionic surfactant. Particularly, it is inferior in compatibility with a base material for gel.

As described above, the conventional resins cannot always satisfy all the performances.

SUMMARY OF THE INVENTION

An object of the present invention is to overcome the above described problems of the conventional hair cosmetic base materials, particularly the problems of an amphoteric ion polymer, and to provide a hair cosmetic composition in which a difficulty in dilution with water upon preparation has been solved and which can be removed thoroughly from hair by washing even when coated on hair and has a good hair conditioning property.

The present inventors have found that the above problems of the conventional hair cosmetic base materials are solved by using a water-soluble resin containing an amine oxide group and having a weight-average molecular weight of 5,000 to 1,000,000.

DETAILED DESCRIPTION OF THE INVENTION

The gist of the present invention resides in a hair cosmetic composition comprising an amine-oxide-containing water-soluble resin having a weight-average molecular weight of 5,000 to 1,000,000.

The amine-oxide-containing resin can be obtained by polymerizing or copolymerizing any one of:

(1) a kind of monomer containing an amine oxide group, (2) two or more kinds of monomers containing an amine oxide group, (3) an amine-oxide-containing monomer and another hydrophilic monomer, and (4) any one of the monomers described in (1) to (3) and a hydrophobic monomer. The amine-oxide-containing monomer is preferably present in an amount of not less than 30% by weight based on the total weight of all the monomers for the water-soluble resin. In the case of (4), the hydrophobic monomer is copolymerized within an extent not damaging the water solubility of the resin. The amine-oxide-containing resin can also be obtained by using a nitrogen-containing precursor monomer instead of the amine-oxide-containing monomer, polymerizing or copolymerizing the monomer, and then subjecting the resultant polymer or copolymer to oxide formation. Alternatively, the amine-oxide-containing resin can be obtained by polymerizing a monomer containing a reaction-active functional group and then allowing to react the resultant polymer with a compound containing both an active group reactive with the functional group and an amine oxide group.

In the present invention, the term "water solubility" as used herein means as follows: when a aqueous solution obtained by stirring one part by weight of an amine-oxide-containing resin and 99 parts by weight of a deionized water under heat at 60° C. for two hours is uniform even after cooling and being allowed to stand for one day at room temperature; and has, in a 1 cm×1 cm cell, a transmittance of 70% or greater at 655 nm, it is regarded to have water solubility.

Hydrophilic monomer (A):

The amine-oxide-containing water-soluble resin usable in the present invention is preferred that the hydrophilic monomer (A) provided for use in the polymerization contains the amine-oxide-containing monomer (a) in an amount of at least 30 wt. %, with the hydrophilic monomer containing the amine-oxide-containing monomer (a) in an amount of at least 50 wt. % being more preferred.

Amine-oxide-containing monomer (a):

Examples of the amine-oxide-containing monomer, which is the component (a), include the monomers represented by the formulas (I) to (IV):

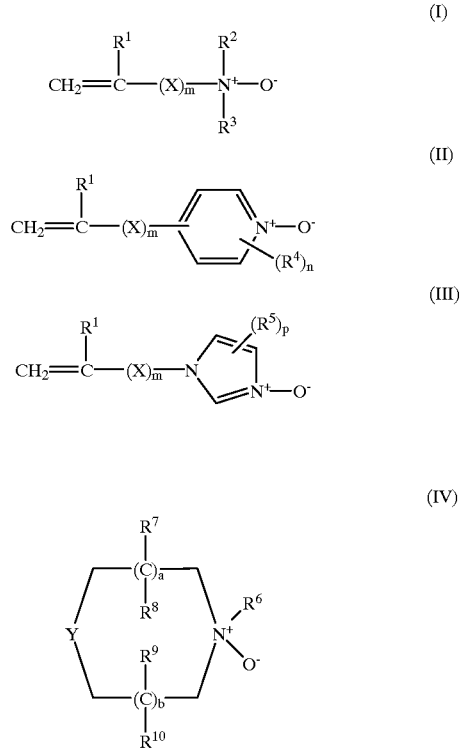

wherein $R^1$ is a hydrogen atom or a methyl group; $R^2$ and $R^3$ are the same or different and each represents a $C_{1-24}$ alkyl, $C_{6-24}$ aryl or $C_{7-24}$ arylalkyl group; $R^4$ and $R^5$ each represents a $C_{1-24}$ alkyl group, a $C_{6-24}$ aryl group or a $C_{7-24}$ arylalkyl group; X represents a divalent binding group; m stands for an integer of 0 or 1; n stands for an integer for 0 to 4; p stands for an integer of 0 to 3; Y represents:

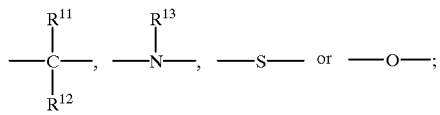

at least one of $R^6$ to $R^{13}$ represents

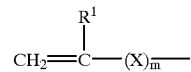

and the other $R^6$–$R^{13}$ each represents a hydrogen atom, a $C_{1-24}$ alkyl group, a $C_{6-24}$ aryl group or a $C_{7-24}$ arylalkyl group; and a and b are the same or different and each represents an integer of 1 to 10.

Examples of the monomer represented by the formula (I) include amine oxides of the compounds such as N,N-dimethylaminoethyl (meth)acrylate, N,N-diethylaminoethyl (meth)acrylate, N,N-dimethylaminopropyl (meth)acrylate, N,N-diethylaminopropyl (meth)acrylate, N,N-dimethylaminoethyl (meth)acrylamide, N,N-diethylaminoethyl (meth)acrylamide, N,N-dimethylaminopropyl (meth)acrylamide, N,N-diethylaminopropyl (meth)acrylamide, vinyl N,N-dimethylaminopropionate, p-dimethylaminomethylstyrene, p-dimethylaminoethylstyrene, p-diethylaminomethylstyrene and p-diethylaminoethylstyrene; and amine oxides of the compounds such as reaction products between an unsaturated-group-containing acid anhydride (e.g., maleic anhydride, itaconic anhydride and crotonic anhydride) and a substance which contains a group reaction-active with the acid anhydride (e.g., N,N-dimethyl-1,3-propanediamine and aniline), and reaction products between an epoxy-containing monomer (e.g., glycidyl methacrylate) and a substance which contains a group reaction-active with the epoxy group (e.g., N,N-dimethyl-1,3-propanediamine). Further examples include products obtained by the reaction between an epoxy-containing monomer such as glycidyl methacrylate and an amine-oxide-containing substance, which contains a group reaction-active with the epoxy group, such as hydroxyethyl-N,N-dimethylamineoxide; and products obtained by the reaction between an isocyanate-containing monomer such as 2-isocyanate ethyl (meth)acrylate and an amine-oxide-containing substance, which contains a group reaction-active with the isocyanate group, such as hydroxyethyl-N,N-dimethylamine oxide.

Examples of the monomer represented by the formula (II) include alkyl-, aryl- and arylalkyl-added amine oxides of the compounds such as 2-vinylpyridine, 3-vinylpyridine, 4-vinylpyridine, 2-methyl-5-vinylpyridine, 3-methyl-5-vinylpyridine, 4-methyl-5-vinylpyridine, 6-methyl-5-vinylpyridine, 2-methyl-4-vinylpyridine, 3-methyl-4-vinylpyridine, 2-lauryl-5-vinylpyridine, 2-lauryl-4-vinylpyridine, 2-(t-butyl)-5-vinylpyridine and 2-(t-butyl)-4-vinylpyridine.

Examples of the monomer represented by the formula (III) include amine oxides of the compounds such as 1-vinylimidazole, 2-methyl-1-vinylimidazole, 4-methyl-1-vinylimidazole, 5-methyl-1-vinylimidazole, 2-lauryl-1-vinylimidazole and 4-(t-butyl)-1-vinylimidazole.

Examples of the monomer represented by the formula (IV) include amine oxides of the compounds such as 4-vinylmorpholine, 2-methyl-4-vinylmorpholine, 4-allylmorpholine, 1-vinylpiperidine, 2-methyl-4-vinylpiperidine, 2-lauryl-1-vinylpiperazine and 4-methylpiperazinoethyl methacrylate.

Of these, the monomers represented by the formula (I) are particularly preferred, with those of the formula (I) in which $R^2$ and $R^3$ each represents a $C_{1-4}$ alkyl group being most preferred.

Nitrogen-containing precursor monomer (b):

The content of the nitrogen-containing precursor monomer is preferably not less than 30 wt. % based on the total weight of all the monomers for the water-soluble resin. Examples of the nitrogen-containing monomer not subjected to oxide formation include the monomers represented by the following formulas (V)–(VIII):

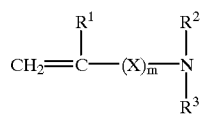
(V)

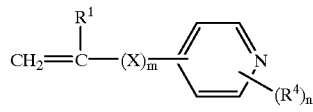
(VI)

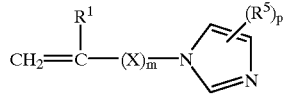
(VII)

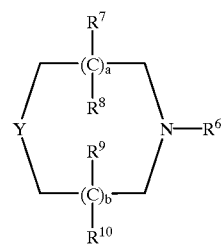
(VIII)

wherein $R^1$–$R^{10}$, a, b, m, n, p, X and Y have the same meanings as defined in the above formulas (I)–(IV).

Other hydrophilic monomers (c):

Examples of such a hydrophilic monomer include nonionic, anionic and cationic monomers and also amphoteric monomers having both anionic and cationic properties in the same molecule.

Of these monomers, specific examples of the nonionic monomer include hydrophilic monomers such as (meth) acrylonitrile, N-cyclohexylmaleimide, N-phenylmaleimide, N-vinylpyrrolidone, N-(meth)acryloylmorpholine, and the monomers derived from a (meth)acrylic acid or (meth) acrylamide and a $C_{2-24}$ alkylene oxide, for example, hydroxyethyl (meth)acrylate, polyethylene glycol (meth) acrylate, methoxypoly(ethylene glycol/propylene glycol) mono(meth)acrylate, polyethylene glycol di(meth)acrylate and N-polyalkyleneoxy (meth)acrylamide; and acrylamide.

Specific examples of the anionic monomer include unsaturated carboxylic acid monomers (e.g., (meth)acrylic acid, maleic acid, maleic anhydride, itaconic acid, fumaric acid and crotonic acid); half esters of an unsaturated polyacid anhydride (e.g., succinic anhydride and phthalic anhydride) with a hydroxy-containing (meth)acrylate (e.g., hydroxyethyl (meth)acrylate); sulfonic-acid-containing monomers (e.g., styrenesulfonic acid and sulfoethyl (meth)acrylate); and phosphoric-acid-containing monomers (e.g., acidphospho-oxyethyl (meth)acrylate).

Each of these anionic unsaturated monomer can be used as an acid or after partial neutralization or complete neutralization. Alternatively, it can be partially neutralized or completely neutralized after being subjected to copolymerization in the form of an acid. Examples of the basic substance used for neutralization include alkali metal hydroxides, for example, potassium hydroxide and sodium hydroxide and amine compounds, for example, aqueous ammonia, mono-, di- and tri-ethanolamines and trimethylamine.

Specific examples of the cationic monomers include those obtained by cationizing N,N-dimethylaminoethyl (meth) acrylate, N,N-diethylaminoethyl (meth)acrylate, N,N-dimethylaminopropyl (meth)acrylate, N,N-diethylaminopropyl (meth)acrylate, N,N-dimethylaminoethyl (meth)acrylamide, N,N-diethylaminoethyl (meth)acrylamide, N,N-dimethylaminopropyl (meth)acrylamide, N,N-diethylaminopropyl (meth)acrylamide, p-dimethylaminomethylstyrene, p-dimethylaminoethylstyrene, p-diethylaminomethylstyrene or p-diethylaminoethylstyrene with a cationizing agent such as an alkyl halide (e.g., methyl chloride, methyl bromide and methyl iodide), a dialkylsulfate (e.g., dimethyl sulfate), an epichlorohydrin-added tertiary amine mineral acid salt (e.g., N-(3-chloro-2-hydroxypropyl)-N,N,N-trimethylammoniumchloride), an inorganic salt (e.g., hydrocholoric acid, hydrobromic acid, sulfuric acid and phosphoric acid), or a carboxylic acid (e.g., formic acid, acetic acid and propionic acid).

Specific examples of the amphoteric unsaturated monomer useful in the present invention include those obtained by modifying the above-exemplified cationic monomers using a modifier, such as sodium haloacetate or potassium haloacetate.

Hydrophobic monomer (B):

Examples of the hydrophobic monomer (B) include hydrophobic vinyl monomers, for example, (meth)acrylate esters of a $C_{1-24}$ alcohol, styrene, p-methylstyrene, p-chlorostyrene, vinyl methyl ether, vinyl cyclohexyl ether, vinyl acetate, diethyl maleate and dibutyl maleate; glycidyl (meth)acrylate; flulroalkyl (meth)acrylate; and unsaturated-group-containing macromonomers, for example, radical-polymerizable unsaturated-group-containing silicon macromonomers.

Specific examples of the (meth)acrylate ester of a $C_{1-24}$ alcohol include methyl (meth)acrylate, ethyl (meth)acrylate, propyl (meth)acrylate, isopropyl (meth)acrylate, butyl (meth)acrylate, isobutyl (meth)acrylate, secondary butyl (meth)acrylate, tertiary butyl (meth)acrylate, pentyl (meth) acrylate, secondary pentyl (meth)acrylate, 1-ethylpropyl (meth)acrylate, 2-methylbutyl (meth)acrylate, isopentyl (meth)acrylate, tertiary pentyl (meth)acrylate, 3-methylbutyl (meth)acrylate, neopentyl (meth)acrylate, hexyl (meth)acrylate, 2-methylpentyl (meth)acrylate, 4-methylpentyl (meth)acrylate, 2-ethylbutyl (meth)acrylate, cyclopentyl (meth)acrylate, cyclohexyl (meth)acrylate, heptyl (meth)acrylate, 2-heptyl (meth)acrylate, 3-heptyl (meth) acrylate, octyl (meth)acrylate, 2-octyl (meth)acrylate, 2-ethylhexyl (meth)acrylate, isooctyl (meth)acrylate, nonyl (meth)acrylate, 3,3,5-trimethylhexyl (meth)acrylate, decyl (meth)acrylate, undecyl (meth)acrylate, lauryl (meth) acrylate, cetyl (meth)acrylate, stearyl (meth)acrylate, eicosyl (meth)acrylate, docosyl (meth)acrylate, tetracosyl (meth) acrylate, methylcyclohexyl (meth)acrylate, isobornyl (meth) acrylate, norbornyl (meth)acrylate, benzyl (meth)acrylate and phenethyl (meth)acrylate.

Of these hydrophobic monomers (B), (meth)acrylate esters of a $C_{1-24}$ alcohol, particularly (meth)acrylate esters of a $C_{1-18}$ alcohol are preferred.

Polymerization ratio of the component (A) to (B):

The preferred content of the hydrophobic monomer (B) varies with the degree of hydrophobicity of the component (B), and the intended use and the used form of the hair cosmetic composition. In general, the content of the component (B) is both not more than 85% by weight of the total weight of the polymer, and within a range not losing the water solubility of the resulting polymer.

Hair cosmetic compositions can be classified roughly into those used for setting and for conditioning.

When used as a setting resin, the hair cosmetic composition of the present invention is preferably a copolymer containing 15–90 wt. % of the component (A) and 85–10 wt. % of the component (B). If the amount of the component (A) is smaller than 15 wt. %, the film of the copolymer could deteriorate in smoothness and transparency, and becomes sparingly-soluble in water so that it sometimes cannot be removed easily upon washing of the hair. If the amount of the component (A) exceeds 90 wt. %, on the other hand, sufficient setting force cannot always be obtained.

The hair cosmetic composition for hair setting is supplied in the form of spray, mousse, gel or the like.

When the hair cosmetic composition is used in the form of spray, it is preferred that the amount of the component (A) is 15–90 wt. % and the amount of the component (B) is 85–10 wt. %, with 30–80 wt. % for the component (A) and 70–20 wt. % for the component (B) being more preferred.

When the hair cosmetic composition is used in the form of mousse, the proportion of water used as a solvent is high so that the composition is required to have a comparatively high hydrophilic property. It is preferred that the amount of the component (A) is 30–90 wt. % and that of the component (B) is 10–70 wt. %, with 40–80 wt. % for the component (A) and 60–20 wt. % for the component (B) being more preferred.

When the hair cosmetic composition is used in the form of gel, the proportion of water is high so that the composition is required to have a proper degree of hydrophilic property, which is similar to the above case in the form of mousse. From the viewpoints of affinity with gel as well as the above-described hydrophilic property, it is preferred that the amount of the component (A) is 40–90 wt. % and that of the component (B) is 60–10 wt. %, with 50–80 wt. % for the component (A) and 50–20 wt. % for the component (B) being more preferred.

When used for hair conditioning, on the other hand, the hair cosmetic composition is required to have high hydrophilic property so as to permit smooth hair touch and easy removal by washing. It is therefore preferred that the amount of the component (A) is 30–100 wt. % and that of the component (B) is 0–70 wt. %, with 50–100 wt. % for the component (A) and 0–50 wt. % for the component (B) being more preferred.

Polymerization process:

Upon preparation of an amine-oxide-containing water-soluble resin of the present invention in practice, any one of the following processes can be employed:

(1) a process in which the nitrogen-containing precursor monomer represented by any one of the formulas (V)–(VIII) is subjected to oxide formation and the resultant amine-oxide-containing monomer is polymerized or copolymerized.

(2) a process in which the nitrogen-containing precursor monomer represented by any one of the formulas (V)–(VIII) is homopolymerized or copolymerized and the resultant nitrogen-containing polymer is subjected to oxide formation.

(3) a process in which a monomer containing a reaction-active functional group is polymerized and then the resultant polymer is reacted with a substance containing both an active group reactive with the functional group and an amine oxide group. Of these three processes, the second one is preferred.

The amine-oxide-containing resin can be obtained by polymerizing the above monomer components generally in the presence of a radical polymerization initiator in a manner known to date, for example, solution polymerization, bulk polymerization or suspension polymerization. In particular, it can be obtained suitably by solution polymerization. Examples of the polymerization solvent include organic solvents, for example, acetone, methyl ethyl ketone, methyl isobutyl ketone, methanol, ethanol, propanol, isopropanol, butanol, isobutanol, secondary butanol, ethyl acetate, propyl acetate and butyl acetate. They may be used either singly or in combination.

Examples of the radical polymerization initiator include azo compounds, such as 2,2'-azobisisobutylonitrile (AIBN), 2,2'-azobis(2,4-dimethylvaleronitrile), 2,2'-azobis(4-methoxy-2,4-dimethylvaleronitrile), dimethyl-2,2'-azobisisobutylate, 2,2'-azobis(2-methylbutylonitrile) and 1,1'-azobis(1-cyclohexanecarbonitrile); and peroxides, such as benzoyl peroxide, dicumyl peroxide, di-t-butyl peroxide and lauroyl peroxide. The polymerization initiator may be used generally in an amount of 0.01 to 5 wt. % based on the total amount of the components (A) and (B).

Polymerization may generally be conducted in an atmosphere of an inert gas, for example, nitrogen or argon at 30° C. to 120° C., preferably 40° C. to 100° C. within 1 to 20 hours.

Oxide formation:

When an amine-oxide-containing water-soluble resin usable in the present invention is prepared in accordance with, for example, the process described in the above (2), it can be prepared by adding an oxide formation agent to the precursor polymer solution, which has been obtained by the polymerization of the monomer components, and then conducting oxide formation at a temperature of from 20° C. to 100° C. for 0.1 to 100 hours, preferably from 1 to 50 hours.

As the oxide formation agent, an oxidizing agent, for example, peroxide or ozone can be employed. Examples of the peroxide include hydrogen peroxide, ammonium persulfate, sodium persulfate, peracetic acid, metachloroperbenzoic acid, benzoyl peroxide, t-butylhydroperoxide and the like. In general, hydrogen peroxide is used in the form of an aqueous solution. The oxide formation agent may be used in an amount of 0.2 to 3 mole equivalents relative to the oxidizable functional group contained in the precursor polymer, with 0.5 to 2 mole equivalents being more preferred. The resin solution so obtained can be used for a hair cosmetic composition without treating the remaining peroxide. It can also be used after being treated in a manner known to date. Specific examples of the treatment include treatment by the addition of a reducing agent, ion-exchange treatment, treatment with activated carbon and treatment with a metallic catalyst.

The resin solution so obtained can be used as is or can be used after isolation of the amine-oxide-containing resin in a manner known to date, for example, by reprecipitation or by distilling off the solvent as needed. The amine-oxide-containing resin so isolated can be further purified, if necessary, by re-precipitation, washing with a solvent, membrane separation, adsorption treatment or the like.

The resin of the present invention so obtained has a weight-average molecular weight of 5,000 to 1,000,000, preferably 10,000 to 500,000, more preferably 20,000 to 300,000. In general, a resin having a comparatively small molecular weight is preferred when used for a hair cosmetic composition for hair setting, while that having a comparatively large molecular weight is preferred when used for conditioning. The same can be said of the resin of the present invention. As resins for hair setting and for hair conditioning, those having a weight-average molecular weight of 5,000 to 300,000 and a weight-average molecular weight of 20,000 to 1,000,000 are preferred, respectively.

Embodiments of the Invention:

As a resin for hair cosmetics, the amine-oxide-containing water-soluble resin for use in the present invention is added to a known hair cosmetic composition, for example, shampoo, hair rinse, treatment agent, setting agent or permanent wave liquid. At this time, it is possible to use in combination with a known, conventionally-employed polymer. The resin can be added to any form of hair cosmetic compositions, such as liquid, cream, emulsion, gel and mousse. The amine-oxide-containing water-soluble resin is preferably added in an amount of 0.01 wt. % to 10 wt. % based on the total amount of the hair cosmetic composition, though depending on the form or the using purpose of the composition, or the kind or amount of the polymer used in combination.

1) Application to hair setting products:

Examples of the hair setting products include known hair conditioning agents containing water and/or an alcohol (e.g., ethanol or isopropanol) as a solvent, such as aerosol hair spray, pump-type hair spray, hair spray foam, hair mist, setting lotion, hair styling, hair cream and hair oil. As a hair cosmetic composition, the amine-oxide-containing resin is used alone or in combination with a known, conventionally-employed, cationic, anionic, nonionic or amphoteric polymer for hair setting.

When used in the form of mousse injectable as a foamed state, the hair cosmetic composition comprises 0.01 wt. % to 10 wt. % of an amine-oxide-containing resin, 0 wt. % to 15 wt. % of a known setting polymer, 0.1 wt. % to 5 wt. % of a nonionic surfactant, 3 wt. % to 25 wt. % of liquefied gas and 60 wt. % to the balance of a water-soluble solvent mainly composed of water (with the proviso that water is contained in an amount of 60 wt. % or greater, based on the total amount of the hair cosmetic composition).

When used in the form of gel, the hair cosmetic composition comprises 0.01 to 10 wt. % of an amine-oxide-containing resin, 0 to 15 wt. % of a known setting polymer, 0.1 to 3 wt. % of a gel base material and 72 wt. % to the balance of water.

When used in the form of hair spray, the hair cosmetic composition comprises 0.01 wt. % to 10 wt. % of an amine-oxide-containing resin, 0 wt. % to 15 wt. % of a known setting polymer, 30 wt. % to 80 wt. % of a solvent and 10 wt. % to 70 wt. % of a propellant.

As the known setting polymer which can be used in combination, examples of the cationic polymer include an ether between hydroxycellulose and glycidyl trimethylammonium chloride ("Leoguard G", trade name; product of Lion Corporation, "Polymer JR-30M-125 and Polymer JR-30M-400"; trade names; products of Union Carbide Corp.), a quaternized copolymer of vinyl pyrrolidone and dimethylaminoethyl methacrylate ("GAFQUAT 734 and 755", trade names; products of GAF Corp.), a dimethyldiallylammonium chloride polymer ("MERQUAT 100", trade name; product of Merck & Co., Ltd.) and dimethyldiallylammonium chloride acryloamide copolymer ("MERQUAT 550", trade name; product of Merck & Co., Ltd.).

Specific examples of the anionic polymer include a copolymer of (meth)acrylic acid and alkyl methacrylate ("Diahold", trade name; product of Mitsubishi Chemical Corp., "Plus Size", trade name; product of GOO Chemical Co., Ltd.), and a copolymer of a monoalkyl maleate and methyl vinyl ether ("GANTREZ", trade name; product of ISP, Inc.).

Examples of the nonionic polymer include a polyvinyl pyrrolidone polymer ("PVP", trade name; product of ISP, Inc.) and a copolymer of vinyl pyrrolidone and vinyl acetate ("LUVISKOL", trade name; product of BASF AG).

Examples of the amphoteric polymer include a methacrylate copolymer ("Yukaformer AM-75W", trade name; product of Mitsubishi Chemical Corp.).

Examples of the nonionic surfactant usable for a mousse include sorbitan fatty acid ester, glycerin fatty acid ester, polyoxyethylene sorbitan fatty acid ester, polyethylene glycol fatty acid ester, polyoxyethylene alkyl ether, polyoxyethylene alkyl phenyl ether, polyoxyethylene castor oil, polyoxyethylene hydrogenated castor oil and fatty acid alkanol amide.

Examples of the propellant for spray include liquefied gas such as liquefied petroleum gas, dimethyl ether and halogenated hydrocarbon; and the compressed gas such as air, carbon dioxide gas and nitrogen gas.

Examples of the liquefied gas for mousse include liquefied petroleum gas, dimethyl ether and halogenated hydrocarbon.

2) Application to the conditioning-function-imparting products:

Hair cosmetic products used to impart hair with a conditioning function include shampoo, hair rinse and permanent liquid, each of which contains water and/or an alcohol (e.g., ethanol or isopropanol) as a solvent; and hair treatment agent which contains water and/or an alcohol (e.g., ethanol and isopropanol) as a solvent, or the alcohol and/or a hydrocarbon having a boiling point of 50° C. to 300° C. Similar to the above-described products for hair setting, as a hair cosmetic composition, the amine oxide-containing resin can be used alone or in combination with a known, conventionally-employed cationic, anionic, nonionic or amphoteric polymer.

When the hair cosmetic composition of the present invention is used as a shampoo, the amine-oxide-containing water-soluble resin is added to a known anionic, amphoteric or nonionic surfactant base material. Concerning the surfactant base material, examples of the anionic surfactant base material include N-fatty acid acyl-N-methyl-β-alanine salt, for example, N-coconoil-N-methyl-β-alanine sodium and N-myristoyl-N-methyl-β-alanine sodium; those of the amphoteric surfactant base material include cocoacid propyl betaine, dimethyl lauryl betaine, bis(2-hydroxyethyl)lauryl betaine, cyclohexyl laurylamine oxide, dimethyl laurylamine oxide and bis(2-hydroxyethyl)laurylamine oxide; and those of nonionic surfactant base material include stearic acid diethanol amide, coconut fatty acid diethanol amide, sorbitan sesquioleate and polyoxyethylene stearyl ether.

When the hair cosmetic composition of the present invention is used as a hair rinse, the amine-oxide-containing water-soluble resin is added to a known cationic surfactant. Examples of the cationic surfactant base material include stearyltrimethylammonium chloride, distearyldimethylammonium chloride and stearyldimethylbenzylammonium chloride.

When the hair cosmetic composition of the present invention is used as a permanent liquid, the amine-oxide-containing water-soluble resin is added to a known oxidizing agent, for example, bromate and perborate, and reducing agent, for example, thioglycolic acid or salt thereof, and cysteine.

When the hair cosmetic composition of the present invention is used as a hair treatment agent, the amine-oxide-containing water-soluble resin is added to a known cationic surfactant base material and/or a cationized polymer, for example, cationic polypeptide, cationic cellulose or cationic polysiloxane. Alternatively, the amine-oxide-containing water-soluble resin may be used singly. As the cationic surfactant base material, those exemplified above in the examples of the hair rinse can also be used for the hair treatment agent.

Optional components:

In either of the products for hair setting or the conditioning-function-imparting products, other optional components, in addition to the above-described various components, can be incorporated, if needed, within a range not affecting the advantage of the present invention.

Exemplary optional components include:

hydrocarbons, such as liquid paraffin, vaseline, solid paraffin, squalane and olefin oligomer;

alcohols, such as linear alcohols (e.g., ethanol, lauryl alcohol, cetyl alcohol, stearyl alcohol, behenyl alcohol, myristyl alcohol, oleyl alcohol and cetostearyl alcohol), and branched alcohols (e.g., monostearyl glycerin ether, 2-decyltetradecinol, lanoline alcohol, cholesterol, phytosterol, hexyldodecanol, isostearyl alcohol and octyldodecanol);

higher fatty acids, such as lauric acid, myristic acid, palmitic acid, stearic acid, behenic (behenyl acid), oleic acid, 1,2-hydroxystearic acid, undecylenic acid, tall acid, lanolic fatty acid, isostearic acid, linolic acid, linoleic acid, γ-linolenic acid and eicosapentaenoic acid and derivatives thereof;

natural water-soluble polymers, such as plant-base polymers (e.g., carrageenan, pectin, agar, quince seed, algae colloid (brown algae extract), starch (rice, corn, potato, wheat) and glycyrrhizinic acid), microorganism-base polymers (e.g., xanthan gum, dextran and pullulan), and animal-base polymers (e.g., collagen and gelatin);

semisynthetic water-soluble polymers, such as cellulose-base polymers (e.g., methyl cellulose, ethyl cellulose, methylhydroxypropyl cellulose, hydroxyethyl cellulose, sodium cellulose sulfate, hydroxypropyl cellulose, sodium carboxymethylcellulose, crystalline cellulose and cellulose powder), and alginic-acid-base polymers (e.g., sodium alginate and propylene glycol alginate);

synthetic water-soluble polymers, such as vinyl-base polymers (e.g., polyvinyl alcohol, polyvinyl methyl ether, polyvinyl pyrrolidone and carboxyvinyl polymer (carbopol)), polyoxyethylene-base polymers (e.g., polyethylene glycols 20,000, 4,000,000 and 600,000, and polyethylene imine);

inorganic water-soluble polymers, such as bentonite, AlMg silicate (bee gum), rabonite, hectorite and silicic anhydride, silicones, such as volatile silicone oil, silicone resin, silicone gum and alkyl-modified silicone;

N-fatty acid acyl-L-glutaminates, such as monosodium N-lauryl-L-glutamate, N-coconut oil fatty acid-L-glutaminic acid monotriethanol amine, monosodium N-myristyric acid acyl-L-glutamate and monosodium N-mixed fatty acid acyl-L-glutamate;

N-fatty acid-N-methyltaurine salts, such as methyl taurine laurate and coconut oil fatty acid methyl taurine sodium, salts of an N-fatty acid sarcosine condensate, such as lauroyl sarcosine sodium and cocoylsarcosine sodium, surfactants, such as acylsarcosine sodium, acylglutaminic acid salt, acyl-β-alanine sodium, acyl taurate, laurylsulfate, lauryldimethylaminoacetic betaine, alkyltrimethyl ammonium chloride and polyoxyethylene hydrogenated castor oil;

sequestering agents, such as 1-hydroxyethane-1,1-diphosphonic acid, tetrasodium 1-hydroxyethane-1,1-diphosphonate, disodium edetate, trisodium edetate, tetrasodium edetate, sodium citrate, sodium polyphosphate, sodium methphosphate and gluconic acid, various ultraviolet absorbers, such as 3-(4'-methylbenzylidene)-d,1-camphor, 3-benzylidene-d,1-camphor, urocanic acid, ethyl urocanate, 2-phenyl-5-methylbenzoxazole, 2,2'-hydroxy-5-methylphenylbenzotriazole, 2- (2'-hydroxy-5'-t-octylphenyl)benzotriazole, 2-(2'-hydroxy-5'-methylphenyl) benzotriazole, dibenzalazine, dianisoylmethane, 4-methoxy-4'-t-butyldibenzoylmethane and 5-(3,3-dimethyl-2-norbornylidene)-3-pentan-2-one, and benzoic acid base-, anthranilic acid base-, salicylic acid base-, cinnamic acid base- and benzophenone base-ultraviolet absorbers;

emulsifiers, such as glyceryl monostearate, sorbitan monopalmitate polyoxyethylene, cetyl ether and polyoxyethylene sorbitan monolaurate;

humectants, such as (poly)ethylene glycol, (poly)propylene glycol, glycerin, 1,3-butylene glycol, maltitol, sorbitol, chondroitin sulfuric acid, hyaluronic acid, aterocollagen, cholesteryl-1,2-hydroxystearate, sodium lactate, bile salt, dl-pyrrolidone carboxylate and short-chain soluble collagen;

antimicrobials, such as hinokithiol, hexachlorophen, benzalconium chloride, trichlorocarbanilide and bithionol, vasodilators, such as carpronium chloride;

reflesh feeling imparting agent, such as menthol;

stimulation imparting agent, such as benzyl nicotinate;

vitamins, such as vitamins A, B, C, D and E;

sterilizing antiseptics, such as chlorohexidine gluconate, isopropyl methyl phenol and paraoxybenzoate;

protein hydrolyzate;

amino acid;

plant extract;

chelating agent, such as EDTA-Na;

Ph regulators, such as succinic acid, sodium succinate and triethanol amine;

foam increasing agent;

foaming agent;

foaming stabilizer;

propellants, such as liquefied petroleum gas and dimethyl ether in the case of an aerosol product;

metal ion scavenger;

antimold;

disinfectant;

emulsion stabilizer;

conditioning agent;

thickener;

antioxidant;

solubilizing agent;

rosin;

hydrotrope;

hair tonic;

crude drug;

colorant; and perfume.

EXAMPLE

The present invention will hereinafter be described more specifically. It should however be borne in mind that the present invention is not limited to or by the following examples.

Preparation Example 1

To a reactor equipped with a reflux condenser, dropping funnel, thermometer, nitrogen gas inlet tube and stirrer, 70 parts by weight of N,N-dimethylaminoethyl methacrylate, 20 parts by weight of N-vinylpyrrolidone, 10 parts by weight of t-butyl methacrylate and 150 parts by weight of anhydrous ethanol were charged, followed by the addition of 0.6 part by weight of 2,2'-azobisisobutylonitrile. The resulting mixture was reacted at 80° C. in a nitrogen gas atmosphere for 8 hours, followed by cooling to 60° C.

To the resulting polymer solution, a 31% aqueous solution containing hydrogen peroxide in an equivalent molar amount of N,N-dimethylaminoethyl methacrylate was added dropwise by the dropping funnel over one hour and stirring was continued for 20 hours, whereby oxide formation of the dimethylamino group was effected. The completion of the oxide formation reaction was confirmed by the measurement of an amine value of the reaction mixture. The polymer so obtained will hereinafter be designated as "P-1".

The resulting polymer had a weight-average molecular weight of 110,000. In addition, the absorption of N-O was recognized as a result of infrared absorption spectrum, whereby the formation of an amine oxide group was confirmed.

Preparation Example 2

To a reactor having a similar structure to that used in Preparation Example 1, 30 parts by weight of N,N-dimethylaminoethyl methacrylate, 70 parts by weight of stearyl methacrylate and 150 parts by weight of anhydrous ethanol were charged, followed by the addition of 0.6 part by weight of 2,2'-azobisisobutylonitrile. The resulting mixture was reacted at 80° C. in a nitrogen gas atmosphere for 8 hours, followed by cooling to 60° C.

To the reaction mixture, a 31% aqueous solution containing hydrogen peroxide in an equivalent molar amount of N,N-dimethylaminoethyl methacrylate was added dropwise over one hour and stirring was continued for 20 hours, whereby oxide formation of the dimethylamino group was effected. The completion of the oxide formation reaction was confirmed by the measurement of an amine value of the reaction mixture. The polymer so obtained will hereinafter be designated as "P-2".

The resulting polymer had a weight-average molecular weight of 100,000. In addition, the absorption of N-O was recognized as a result of infrared absorption spectrum, whereby the formation of an amine oxide group was confirmed.

Preparation Example 3

To a reactor having a similar structure to that used in Preparation Example 1, 40 parts by weight of N,N-dimethylaminopropyl methacrylamide, 30 parts by weight of methyl methacrylate, 25 parts by weight of t-butyl methacrylate, 5 parts by weight of "Polysiloxane FM0721", 0.6 part by weight of 2,2'-azobisisobutylonitrile and 150 parts by weight of anhydrous ethanol were charged, followed by heating at 80° C. under reflux in a nitrogen gas atmosphere. The polymerization was conducted for further 10 hours.

To the polymer solution so obtained, a 31% aqueous solution of hydrogen peroxide containing 1.2 times the molar amount of N,N-dimethylaminopropyl methacrylamide was added dropwise over one hour by the dropping funnel and stirring was continued for 10 hours, whereby oxide formation of the dimethylamino group was effected. The completion of the oxide formation reaction was confirmed by the measurement of an amine value of the reaction mixture. The polymer so obtained will hereinafter be designated as "P-3".

The resulting polymer had a weight-average molecular weight of 80,000. In addition, the absorption of N-O was recognized as a result of infrared absorption spectrum, whereby the formation of an amine oxide group was confirmed.

Preparation Example 4

To a reactor having a similar structure to that used in Preparation Example 1, 50 parts by weight of N,N-dimethylaminoethyl methacrylate, 50 parts by weight of t-butyl methacrylate and 150 parts by weight of anhydrous ethanol were charged, followed by the addition of 0.6 part by weight of 2,2'-azobisisobutylonitrile. In a nitrogen gas atmosphere, the resulting mixture was heated to 80° C. over 40 minutes and reacted at 80° C. for 8 hours, followed by cooling to 60° C.

To the reaction mixture, a 31% aqueous solution containing hydrogen peroxide in an equivalent molar amount of N,N-dimethylaminoethyl methacrylate was added dropwise over one hour and stirring was continued for 20 hours, whereby oxide formation of the dimethylamino group was effected. The completion of the oxide formation reaction was confirmed by the measurement of an amine value of the reaction mixture. The polymer so obtained will hereinafter be designated as "P-4".

The resulting polymer had a weight-average molecular weight of 100,000. In addition, the absorption of N-O was recognized as a result of infrared absorption spectrum, whereby the formation of an amine oxide group was confirmed.

Preparation Example 5

To a reactor having a similar structure to that used in Preparation Example 1, 100 parts by weight of N,N-dimethylaminoethyl methacrylate and 150 parts by weight of anhydrous ethanol were charged, followed by the addition of 0.1 part by weight of 2,2'-azobisisobutylonitrile. In a nitrogen gas atmosphere, the resulting mixture was heated to 80° C. over 40 minutes and then reacted at 80° C. for 8 hours, followed by cooling to 60° C.

To the reaction mixture, a 31% aqueous solution containing hydrogen peroxide in 1.2 times the molar amount of N,N-dimethylaminoethyl methacrylate was added dropwise over one hour and stirring was continued for 20 hours, whereby oxide formation of the dimethylamino group was effected. The completion of the oxide formation reaction was confirmed by the measurement of an amine value of the reaction mixture. The polymer so obtained will hereinafter be designated as "P-5".

The resulting polymer had a weight-average molecular weight of 20,000. In addition, the absorption of N-O was recognized as a result of infrared absorption spectrum, whereby the formation of an amine oxide group was confirmed.

Preparation Example 6

To a reactor having a similar structure to that used in Preparation Example 1, 80 parts by weight of N,N-dimethylaminoethyl methacrylate, 20 parts by weight of butyl methacrylate and 150 parts by weight of anhydrous ethanol were charged, followed by the addition of 0.6 part by weight of 2,2'-azobisisobutylonitrile. In a nitrogen gas atmosphere, the resulting mixture was reacted at 80° C. for 8 hours, followed by cooling to 60° C.

To the reaction mixture, a 31% aqueous solution containing hydrogen peroxide in 0.5 time the molar amount of N,N-dimethylaminoethyl methacrylate was added dropwise over one hour and stirring was continued for 20 hours, whereby oxide formation of the dimethylamino group was effected. The completion of the oxide formation reaction was confirmed by the measurement of an amine value of the reaction mixture. The polymer so obtained will hereinafter be designated as "P-6".

The resulting polymer had a weight-average molecular weight of 110,000. In addition, the absorption of N-O was recognized as a result of infrared absorption spectrum, whereby the formation of an amine oxide group was confirmed.

Preparation Example 7

To a reactor having a similar structure to that used in Preparation Example 1, 45 parts by weight of N,N-dimethylaminoethyl methacrylate, 35 parts by weight of octyl methacrylate, 20 parts by weight of butyl acrylate and 150 parts by weight of anhydrous ethanol were charged, followed by the addition of 0.6 part by weight of 2,2'-azobisisobutylonitrile. In a nitrogen atmosphere, the resulting mixture was reacted at 80° C. for 8 hours, followed by cooling to 60° C.

To the reaction mixture, a 31% aqueous solution containing hydrogen peroxide in 0.5 time the molar amount of N,N-dimethylaminoethyl methacrylate was added dropwise over one hour and stirring was continued for 20 hours, whereby oxide formation of the dimethylamino group was effected. Then, monochloroacetic acid neutralized with potassium hydroxide, which had been prepared in advance, was added in 0.5 time the molar amount of N,N-dimethylaminoethyl methacrylate to the reactor by the dropping funnel. The reactor was maintained at 80° C. in a nitrogen gas atmosphere for 20 hours, whereby a reaction for the conversion into a corresponding amphoteric polymer was conducted. The completion of the conversion reaction was confirmed by the measurement of an amine value of the reaction mixture. The polymer so obtained will hereinafter be designated as "P-7".

The resulting polymer had a weight-average molecular weight of 110,000. In addition, the absorption of N-O was recognized as a result of infrared absorption spectrum, whereby the formation of an amine oxide group was confirmed.

Preparation Example 8

To a reactor having a similar structure to that used in Preparation Example 1, 80 parts by weight of N,N-dimethylaminoethyl methacrylate, 20 parts by weight of stearyl methacrylate and 150 parts by weight of anhydrous ethanol were charged, followed by the addition of 1.0 part by weight of 2,2'-azobisisobutylonitrile. In a nitrogen atmosphere, the resulting mixture was reacted at 80° C. for 8 hours, followed by cooling to 60° C.

To the reaction mixture, a 31% aqueous solution containing hydrogen peroxide in 1.5 times the molar amount of the N,N-dimethylaminoethyl methacrylate was added dropwise over one hour and stirring was continued for 20 hours, whereby oxide formation of the dimethylamino group was effected. The completion of the oxide formation reaction was confirmed by the measurement of an amine value of the reaction mixture. The polymer so obtained will hereinafter be designated as "P-8".

The resulting polymer had a weight-average molecular weight of 50,000. In addition, the absorption of N-O was recognized as a result of infrared absorption spectrum, whereby the formation of an amine oxide group was confirmed.

Preparation Example 9

To a reactor having a similar structure to that used in Preparation Example 1, 5 parts by weight of N,N-dimethylaminoethyl methacrylate, 80 parts by weight of stearyl methacrylate, 15 parts by weight of ethyl methacrylate and 150 parts by weight of butanol were charged, followed by the addition of 0.6 part by weight of 2,2'-azobisisobutylonitrile. In a nitrogen atmosphere, the resulting mixture was reacted at 80° C. for 8 hours, followed by cooling to 60° C.

To the reaction mixture, a 31% aqueous solution containing hydrogen peroxide in an equivalent molar amount of the N,N-dimethylaminoethyl methacrylate was added dropwise over one hour and stirring was continued for 20 hours, whereby oxide formation of the dimethylamino group was effected. The completion of the oxide formation reaction was confirmed by the measurement of an amine value of the reaction mixture. The polymer so obtained will hereinafter be designated as "P-9".

The resulting polymer had a weight-average molecular weight of 150,000. In addition, the absorption of N-O was recognized as a result of infrared absorption spectrum, whereby the formation of an amine oxide group was confirmed.

Preparation Example 10

To a reactor having a similar structure to that used in Preparation Example 1, 20 parts by weight of N,N-dimethylaminoethyl methacrylate, 30 parts by weight of lauryl methyacrylate, 50 parts by weight of fluoroalkyl methacrylate ("Lightester FM-108", trade name; product of Kyoeisha Chemical Co., Ltd.) and 150 parts by weight of butanol were charged, followed by the addition of 0.6 part by weight of 2,2'-azobisisobutylonitrile. In a nitrogen gas atmosphere, the resulting mixture was reacted at 80° C. for 8 hours, followed by cooling to 60° C.

To the reaction mixture, a 31% aqueous solution containing hydrogen peroxide in 1.2 times the molar amount of the N,N-dimethylaminoethyl methacrylate was added dropwise over one hour and stirring was continued for 20 hours to conduct oxide formation of the dimethylamino group. The completion of the oxide formation reaction was confirmed by the measurement of an amine value of the reaction mixture. The polymer so obtained will hereinafter be designated as "P-10".

The resulting polymer had a weight-average molecular weight of 100,000. In addition, the absorption of N-O was recognized as a result of infrared absorption spectrum, whereby the formation of an amine oxide group was confirmed.

The water solubility of each of the polymers "P-1" through "P-10" obtained in Preparation examples 1 through 10 was measured. The results are shown in Table 1. The measurement method and evaluation standards were conducted as follows:

<Water solubility>

One part by weight of a polymer and 99 parts by weight of deionized water are stirred under heat at 60° C. for 2 hours. The aqueous solution so obtained is allowed to stand for one day after cooling and its transmittance at a wavelength of 655 nm in a 1 cm×1 cm cell is measured. The water solubility is ranked as A, B and C when the tranmittances are 70 to 100%, 30 to 70% and 0 to 30%, respectively.

TABLE 1

| Polymer | Water solubility |
| --- | --- |
| P-1 | A |
| P-2 | A |
| P-3 | A |
| P-4 | A |
| P-5 | A |
| P-6 | A |
| P-7 | A |
| P-8 | A |
| P-9 | C (precipitates were formed) |
| P-10 | C (precipitates were formed) |

Example 1

The following shampoo composition was prepared.

| | (wt. %) |
| --- | --- |
| Sodium polyoxyethylenelaurylsulfate (3EO adduct) | 16% |
| Lauroyl diethanolamide | 2% |
| "P-1" | 1.5% |
| Perfume | 0.2% |
| Antiseptic | 0.1% |
| Colorant | trace |
| Water | balance 100% |

The application of this composition as a shampoo has made it possible to comb hair easily even after washing and to impart dried hair with excellent luster and gloss, smooth touch and easy combing. Even the use of this shampoo in repetition did not give an adverse effect, for example stickiness, to hair.

The shampoo compositions obtained by using "P-4", "P-5", "P-6", "P-8" in stead of "P-1" showed excellent results, respectively, similar to the above.

Comparative Example 1

In a similar manner to Example 1 except for the use of "P-9" and "P-10" instead of "P-1", shampoo compositions were prepared, respectively. When used as shampoos, owing to the inferior water solubility, they did not impart the dried hair with any of luster, gloss and smooth touch and moreover, hair could not be combed easily.

Example 2

The following hair rinse composition was prepared.

|  | (wt. %) |
| --- | --- |
| Stearyltrimethylammonium chloride | 1.5% |
| Cetanol | 2% |
| "P-2" | 1.5% |
| Perfume | 0.2% |
| Pure water | balance |
|  | 100% |

The application of this composition as a hair rinse has made it possible to comb hair easily after rinsing and to impart dried hair with excellent luster and gloss, smooth touch and easy combing. Even the use of this rinse composition in repetition did not give an adverse effect, for example stickiness, to the hair.

The hair rinse compositions which contain "P-1", "P-3", "P-4", "P-5", "P-6" and "P-8" in stead of "P-2" also showed excellent results, respectively similar to the above.

Comparative Example 2

In a similar manner to Example 2 except for the use of "P-9" and "P-10" instead of "P-2", the hair rinse compositions were prepared, respectively. When used as a hair rinse, they did not impart the dried hair with any one of luster, gloss and smooth touch owing to the inferior water solubility and moreover, hair could not be combed easily.

Example 3

The following diluted stock solution was charged in a spray bottle, followed by filling with liquefied petroleum gas, whereby a hair spray composition was prepared.

| Diluted stock solution | (wt. %) |
| --- | --- |
| "P-2" | 4% |
| Anhydrous ethanol | 46% |
|  | 50% |
| Liquefied petroleum gas (3 kgf/cm$^2$, 20° C.) | 50% |

The application of this composition to hair by spray coating has made it possible to impart hair with excellent set retention and in addition, with excellent luster and gloss and smooth touch.

The similar results could be obtained in the compositions using the polymers "P-1", "P-3", "P-4", "P-6", "P-7" and "P-8" instead of "P-2", respectively.

Comparative Example 3

In a similar manner to Example 3 except for the use of "P-9" and "P-10" instead of "P-3", the compositions were prepared, respectively. When used by spray coating, their set retention of hair was weak and they did not impart the hair with any of luster, gloss and smooth touch.

Example 4

The following foamed aerosol composition was prepared in a similar manner to Example 3.

| Diluted stock solution | (wt. %) |
| --- | --- |
| "P-3" | 2% |
| Carboxybetaine-type amphoteric polymer ("Yukaformer AM-75-R 205S", trade name; product of Mitsubishi Chemical Corp.) | 2% |
| Polyoxyethylene cetyl ether (10EO adduct) | 0.3% |
| Polyoxyethylene cetyl ether (2EO adduct) | 0.1% |
| Pure water | balance (83.6%) |
|  | 88% |
| Liquefied petroleum gas (3 kgf/cm$^2$, 20° C.) | 12% |

When this composition was applied to hair by spray coating, it showed excellent results similar to Example 3.

The compositions which contain "P-1", "P-2", "P-4", "P-6", "P-7" and "P-8" in stead of "P-3" also showed excellent results, respectively similar to the above.

Comparative Example 4

In a similar manner to Example 4 except for the use of "P-9" and "P-10" instead of "P-3", the compositions were prepared, respectively. When they were used by spray coating, their set retention could not be evaluated owing to the inferior water solubility and they did not impart hair with any of luster, gloss and smooth touch.

Example 5

The following setting lotion was prepared.

|  | (wt. %) |
| --- | --- |
| "P-4" | 3% |
| Pure water | 60% |
| Anhydrous ethanol | balance (37%) |
|  | 100% |

When this composition was applied to hair, it showed excellent results similar to Example 4.

The compositions which contain polymers "P-1", "P-2", "P-3", "P-6", "P-7" and "P-8" in stead of "P-4" also showed excellent results, respectively, similar to the above.

Comparative Example 5

In a similar manner to Example 5 except for the use of "P-9" and "P-10" instead of "P-4", the compositions were prepared, respectively. When used as a setting lotion, they showed weak set retention to hair and in addition, they did not impart hair with any of luster, gloss and smooth touch.

Example 6

The following gel composition was prepared.

|  | (wt. %) |
| --- | --- |
| "P-4" | 2% |
| Gel Base ("Carbopol 940", trade name; | 0.5% |

-continued

| | (wt. %) |
|---|---|
| product of B. F. Goodrich Chemical Co., Ltd.) | |
| Pure water | balance (97.5%) |
| | 100% |

When the above composition was used for hair as a gel, it imparted hair with excellent set retention, and also with excellent luster, gloss and smooth touch. Even when application and washing of the gel composition were repeated, it did not bring about adverse effects, for example, a feeling of physical disorder caused by stickiness, accumulation or the like.

The compositions which contain the polymers "P-1", "P-2", "P-3", "P-6", "P-7" and "P-8" instead of "P-4" showed similar results to the above, respectively.

Comparative Example 6

In a similar manner to Example 6 except for the use of the polymers "P-9" and "P-10" instead of "P-4", the compositions were obtained, respectively. When they were used as a gel, owing to inferior solubility in water, set retention could not be evaluated and they did not impart hair with any of luster, gloss and smooth touch.

Comparative Example 7

To a five-neck flask equipped with a reflux condenser, dropping funnel, thermometer, nitrogen gas purging glass tube and stirrer, 90 parts by weight of N,N-dimethylaminoethyl methacrylate, 70 parts by weight of butyl methacrylate, 40 parts by weight of lauryl methacrylate and 200 parts by weight of ethyl alcohol, followed by the addition of 1.2 parts by weight of $\alpha,\alpha'$-azobisisobutylonitrile. The resulting mixture was heated at 80° C. under reflux while being purged with a nitrogen gas and polymerization was conducted for 4 hours.

To a solution of 54 parts by weight of monochloroacetic acid dissolved in 110 parts by ethanol, 56 parts by weight of cyclohexylamine were added to neutralize the monochloroacetic acid. The solution so neutralized was added dropwise to the flask through the dropping funnel. The reaction mixture was maintained at 80° C. for 4 hours under a nitrogen gas stream, whereby conversion into an amphoteric polymer was conducted. As a result, a highly viscous solution having a resin content of 50 parts by weight was obtained.

The water solubility of the resultant polymer was measured in a similar manner employed for Preparation Examples 1 through 10. The polymer showed a good transmittance as high as 70% or greater.

A hair gel composed of 4 wt. % of the highly-viscous solution, 0.5 wt. % of a gel base and the balance (95.5 wt. %) of pure water was prepared and evaluated as in Example 6. The results are shown in Table 2.

The evaluation was conducted in accordance with the following manner.

(1) Setting force

After a bundle of hairs having a length of 23 cm and a weight of 2.0 g was soaked in the gel composition, it was taken out, squeezed weakly, wound round a rod having a diameter of 1 cm and then dried. The rod was then removed from the curled bundle. The bundle so curled was hung in an air-conditioned box, which had been controlled to 20° C. and 80% humidity over three hours in advance, for 30 minutes. From the observation of the loosening state of the curled bundle, setting force was judged.

A: almost no change.
B: A slight loosening was recognized.
C: An apparent loosening was recognized.

(2) Transmittance

The transmittance of the gel composition at 655 nm in a 1 cm×1 cm cell was measured.

TABLE 2

| | Setting force | Transmittance (%) |
|---|---|---|
| Example 6 | A | 90 |
| Comparative Example 7 | B | 5 |

From Table 2, it is understood that the gel composition according to the present invention has a much higher transmittance than a gel composition using the conventional amphoteric ion polymer. This is because the amine-oxide-containing water soluble resin is much more compatible with base materials for hair cosmetics (e.g., a gel base) than the conventional amphoteric ion polymer so that the application of the water-soluble resin of the present invention to a gel composition cause no turbidity.

The present invention has made it possible to provide various hair cosmetic compositions in the form of, for example, hair spray, mousse, setting lotion and gel which compositions have excellent adhesion to hair, good setting force and conditioning effects and also impart hair with good touch of feeling.

While the invention has been described in detail and with reference to specific embodiments thereof, it will be apparent to one skilled in the art that various changes and modifications can be made therein without departing from the spirit and scope thereof.

What is claimed is:

1. A hair cosmetic composition comprising an amine-oxide-containing water-soluble resin having a weight average molecular weight (Mw) of 5,000 to 1,000,000.

2. A hair cosmetic composition according to claim 1, wherein said water-soluble resin has a weight-average molecular weight of 10,000 to 500,000.

3. A hair cosmetic composition according to claim 1, wherein said water-soluble resin has a weight-average molecular weight of 20,000 to 300,000.

4. A hair cosmetic composition according to claim 1, wherein said water-soluble resin is obtained by polymerizing:

(A) 15 to 100 wt. % of a hydrophilic monomer including an amine-oxide-containing monomer, and (B) 85 to 0 wt. % of a hydrophobic monomer.

5. A hair cosmetic composition according to claim 4, wherein said water-soluble resin is obtained by polymerizing:

(A) 15 to 90 wt. % of a hydrophilic monomer including an amine-oxide-containing monomer, and (B) 85 to 10 wt. % of a hydrophobic monomer;

and said cosmetic composition is suitable for use in hair setting.

6. A cosmetic hair composition according to claim 5, wherein said cosmetic composition is supplied in the form of spray.

7. A cosmetic hair composition according to claim 5, wherein said water-soluble resin is obtained by polymerizing:

(A) 30 to 90 wt. % of a hydrophilic monomer including an amine-oxide-containing monomer, and (B) 70 to 10 wt. % of a hydrophobic monomer;

and said cosmetic composition is supplied in the form of mousse.

8. A cosmetic hair composition according to claim 5, wherein said water-soluble resin is obtained by polymerizing:

(A) 40 to 90 wt. % of a hydrophilic monomer including an amine-oxide-containing monomer, and (B) 60 to 10 wt. % of a hydrophobic monomer;

and said cosmetic composition is supplied in the form of a gel.

9. A cosmetic hair composition according to claim 4, wherein said water-soluble resin is obtained by polymerizing:

(A) 30 to 100 wt. % of a hydrophilic monomer including an amine-oxide-containing monomer, and (B) 70 to 0 wt. % of a hydrophobic monomer;

and said cosmetic composition is suitable for use in hair conditioning.

10. A hair cosmetic composition according to claim 4, wherein said amine-oxide-containing monomer of the component (A) is an amine-oxide-containing ethylenically-unsaturated monomer.

11. A hair cosmetic composition according to claim 4, wherein said amine-oxide-containing monomer of the component (A) is a compound represented by a formula selected from the group consisting of the following formulas (I) to (IV):

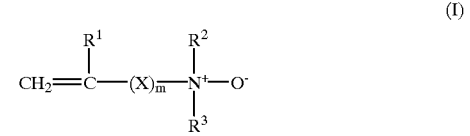
(I)

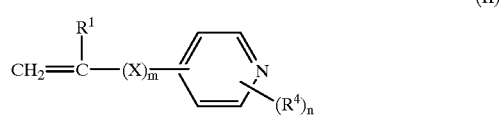
(II)

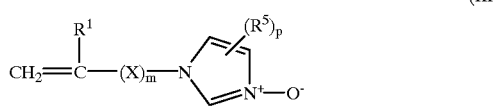
(III)

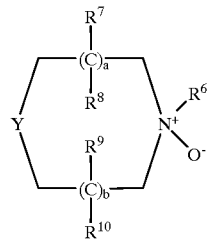
(IV)

wherein $R^1$ is a hydrogen atom or a methyl group; $R^2$ and $R^3$ are the same or different and each represents a $C_{1-24}$ alkyl group, a $C_{6-24}$ aryl group or a $C_{7-24}$ arylalkyl group; $R^4$ and $R^5$ each represents a $C_{1-24}$ alkyl group, a $C_{6-24}$ aryl group or a $C_{7-24}$ arylalkyl group; X represents a divalent binding group; m stands for an integer of 0 or 1; n stands for an integer of 0 to 4; p stands for an integer of 0 to 3; Y represents:

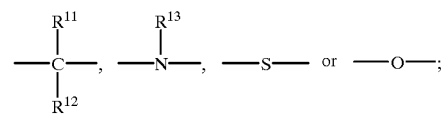

at least one of $R^6$ to $R^{13}$ represents

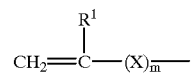

and the other $R^6$ to $R^{13}$ each represents a hydrogen atom, a $C_{1-24}$ alkyl group, a $C_{6-24}$ aryl group or a $C_{7-24}$ arylalkyl group; and a and b are the same or different and each represents an integer of 1 to 10.

12. A hair cosmetic composition according to claim 4, wherein the hydrophobic monomer of the component (B) is an alkyl ester of acrylic acid or methacrylic acid, said alkyl group having 1 to 24 carbon atoms.

13. A hair cosmetic composition according to claim 4, wherein the hydrophilic monomer of the component (A) other than the amine-oxide-containing monomer is selected from the group consisting of acrylic acid and derivatives thereof, methacrylic acid and derivatives thereof, acrylamide and derivatives thereof, methacrylamide and derivatives thereof, and styrene derivatives.

14. A hair cosmetic composition according to claim 4, wherein the amine-oxide-containing monomer is present in an amount of not less than 30 wt. % based on the total weight of the component (A).

15. A hair cosmetic composition according to claim 4, wherein the amine-oxide-containing monomer is present in an amount of not less than 50 wt. % based on the total weight of the component (A).

16. A hair cosmetic composition according to claim 4, wherein the amine-oxide-containing monomer is present in an amount of not less than 30 wt. % based on the total weight of all the monomers for the water-soluble resin.

17. A hair cosmetic composition according to claim 1, wherein said water-soluble resin has been obtained by polymerizing a monomer containing a nitrogen-containing precursor monomer and then subjecting the resultant polymer to oxide formation.

18. A hair cosmetic composition according to claim 17, wherein said nitrogen-containing precursor monomer is an ethylenically unsaturated monomer.

19. A hair cosmetic composition according to claim 17, wherein said nitrogen-containing precursor monomer is a compound represented by a formula selected from the group consisting of the following formulas (V) to (VIII):

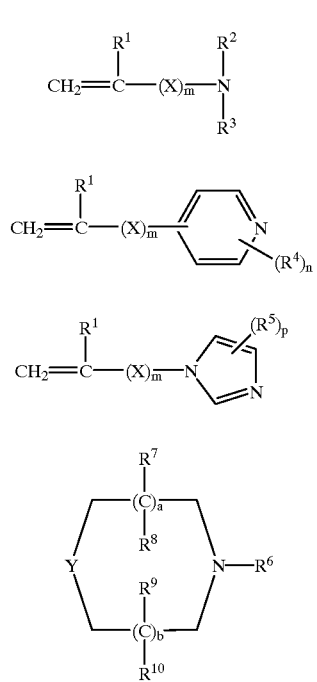

wherein $R^1$ is a hydrogen atom or a methyl group; $R^2$ and $R^3$ are the same or different and each represents a $C_{1-24}$ alkyl group, a $C_{6-24}$ aryl group or a $C_{7-24}$ arylalkyl group; $R^4$ and $R^5$ each represents a $C_{1-24}$ alkyl group, a $C_{6-24}$ aryl group or a $C_{7-24}$ arylalkyl group; X represents a divalent binding group; m stands for an integer for an integer of 0 or 1; n stands for an integer of 0 to 4; p stands for an integer of 0 to 3; Y represents:

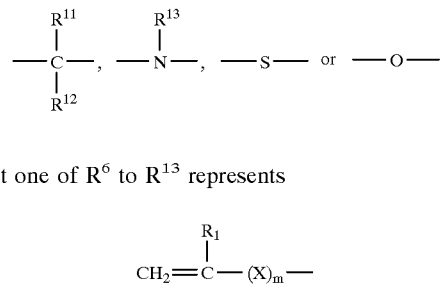

at least one of $R^6$ to $R^{13}$ represents $$CH_2{=}\overset{R_1}{\underset{|}{C}}{-}(X)_m{-}$$

and other $R^6$ to $R^{13}$ each represents a hydrogen atom, a $C_{1-24}$ alkyl group, a $C_{6-24}$ aryl group or a $C_{7-24}$ arylalkyl group; and a and b are the same or different and each represents an integer of 1 to 10.

20. A hair cosmetic composition according to claim 17, wherein the nitrogen-containing precursor monomer is present in an amount of not less than 30 wt. % based on the total weight of all the monomers for the water-soluble resin.

21. A hair cosmetic composition according to claim 1, which comprises 0.01 to 10 wt. % of said water-soluble resin.

* * * * *